United States Patent [19]
Dordick et al.

[11] Patent Number: 5,270,460
[45] Date of Patent: Dec. 14, 1993

[54] SUCROSE 6,4'-DICARBOXYLIC ESTERS

[75] Inventors: Jonathan S. Dordick, Iowa City, Iowa; Andrew J. Hacking, Mortimer; Riaz A. Khan, Sonning, both of Great Britain

[73] Assignee: Tate & Lyle Public Limited Company, Great Britain

[21] Appl. No.: 893,407

[22] Filed: Jun. 3, 1992

Related U.S. Application Data

[62] Division of Ser. No. 412,904, Sep. 26, 1989, Pat. No. 5,128,248.

[30] Foreign Application Priority Data

Sep. 27, 1988 [GB] United Kingdom ................ 8822673

[51] Int. Cl.$^5$ ............................................. C07H 11/00
[52] U.S. Cl. ................................. 536/115; 536/119; 536/122; 435/100
[58] Field of Search ................ 435/100; 536/122, 119, 536/115

[56] References Cited

U.S. PATENT DOCUMENTS 4,405,654  9/1983  Lee ....................................... 536/122
4,889,928  12/1989  Simpson ............................... 536/122

OTHER PUBLICATIONS

Fiegapane et al., *Enz. Microb. Technol.*, vol. 13, Oct. 1991, pp. 796–800.

*Primary Examiner*—Ronald W. Griffin
*Assistant Examiner*—Pamela S. Webber
*Attorney, Agent, or Firm*—Ostrolenk, Faber, Gerb & Soffen

[57] ABSTRACT

Sucrose or derivatives thereof such as esters are acylated at the 4'- and/or the 6- position by reaction with a donor acyl ester, e.g. a reactive ester of an alkanoic acid or benzoic acid, in the presence of lipase. Sucrose 6,4' so produced can be chlorinated and deacylated to produce the sweetener sucralose.

3 Claims, No Drawings

SUCROSE 6,4'-DICARBOXYLIC ESTERS

This is a division of application Ser. No. 07/412,904, filed Sep. 26, 1989, now U.S. Pat. No. 5,128,248.

This invention relates to a method for the selective acylation of sucrose and sucrose derivatives which are useful as intermediates in the production of the high intensity sweetener sucralose (4,1', 6'-trichloro-4,1', 6'-trideoxy galactosucrose) which is about 600 times sweeter than sucrose. The use of sucralose and other chlorodeoxy sucrose derivatives is disclosed in our British Patents No. 1,543,167 and No. 2,104,063B.

The invention also relates to novel acylated derivatives of sucrose.

Routes to sucralose (see, for example Khan et al Carbohydrate Research, 39 (1975) 253; Fairclough et al Carbohydrate Research, 40 (1975) 285–289; U.S. Pat. No. 4,362,869 and G.B Patent No. 2,065,648) involve the formation of sucrose derivatives in which the 6-position is blocked so as to prevent chlorination in that position while the 4-, 1'- and 6'- positions are chlorinated. In the route of U.S. Pat. No. 4,362,869 and Fairclough, sucrose is tritylated in the three primary positions (6-, 1'- and 6') and peracetylated. The trityl groups are then removed to provide the 2,3,4,3',4'-pentaacetate and the acetate at the 4-position is caused to migrate to the 6- position, in the case of the patented process by treatment with dilute acetic acid in an inert solvent, so as to provide the desired 2,3,6,3'-4'-pentaacetate, which can then be chlorinated and deacetylated to yield sucralose.

Another simpler method, involving fewer steps (see for example, U.S. Pat. No. 4,380,476 and G.B Patent No. 2,079,749), comprises the selective acylation of sucrose at the 6- position, followed by the selective chlorination of 4-,1'- and 6'- positions in the presence of unprotected hydroxy groups at the 2-, 3-, 3'- and 4'-positions. However, neither the selective acylation nor the selective chlorination are easy to perform, and traces of unwanted chlorodeoxy sucrose derivatives, such as 4,1',4', 6'-tetrachloro-4,1', 4',6'-tetradeoxy sucrose, may occur in the final product.

Thus, there remains a need for a simple process for the production of sucralose in a few steps which can provide a purer product.

A more satisfactory alternative to the 6-acylated intermediate might be a di-acylated sucrose, particularly one in which the 6- and 4'-positions are protected. Protection of the relatively reactive 4'-position as well as the 6-position should enhance the selectivity of the chlorination process. However, hitherto 6,4'-sucrose acylates have not been accessible.

Therisod and Klibanov (J American Chemical Society 1986, 108, 5638-5640) showed that porcine pancreatic lipase regioselectively acylates the primary hydroxy group of monosaccharides in pyridine. However, this enzyme was virtually unreactive with di- and oligosaccharides. Further, most of the enzymes that they tested were catalytically inactive in pyridine and dimethylformamide which are the best hydrophilic organic solvents for sugars.

Surprisingly, we have now found that sucrose and derivatives thereof can be acylated selectively, to obtain the 6,4'-diester, using lipases.

According to the present invention we provide a process for acylating sucrose or a derivative thereof at the 4'- and/or 6- positions by reaction with a donor acyl ester in a non-hydroxylic solvent in the presence of a lipase.

According to the present invention we also provide as new compounds the 6,4'-diacetate, dibenzoate and dibutyrate of sucrose specifically, and sucrose 6,4'-diesters of carboxylic acids generally.

The donor acyl ester is conveniently a reactive ester of an alkanoic acid or benzoic acid, e.g. an isopropenyl or trichloroethyl ester. The alkanoic acid is preferably $C_2$-$C_5$ alkanoic acid, e.g. acetic, propionic or butyric acid. In general, the ester should be present in a substantial excess over the theoretical one or two equivalents required for mono- or di-esterification respectively. Typically a ratio of about 2.5 to 12.5 ME of ester per ME of sucrose or sucrose derivative is effective.

The solvent is conveniently an amine or amide, particularly an aromatic tertiary amine such as pyridine, lutidine or picoline, or an N,N-dialkylamide such as dimethylformamide or dimethylacetamide. The concentration of the sucrose or sucrose derivative in the solvent can generally be from about 5% w/v to about 40% w/v and will depend, in part, on the solubility. There is no need to add water.

The starting material is either sucrose itself (in the preparation of sucrose 6,4'-diesters) or a derivative, especially a sucrose ester with one or both of the 6- and 4'-positions unesterified. Thus, for example, sucrose 6-esters can be esterified at the 4'-position by this route to provide the corresponding 6,4'-diester. Other positions may also be esterified, e.g. any of the 2-, 3- and 3'-positions, but (for sucralose production) the 4-, 1'- and 6'-positions must be free. In particular, reaction with sucrose 2,3,3',4'-tetraacetate gives the 2,3,6,3',4'-pentaacetate, known as 6-PAS, which is a key intermediate in the sucralose process of U.S. Pat. No. 4,362,869.

The enzyme should be present in a quantity of at least about 20 units up to about 100 units per mg of sucrose or derivative. The actual weight of enzyme will depend on the purity. For example the commercial Lipase P Amano contains only about 30 units per mg, as compared with 20,000 to 50,000 for some highly pure enzymes.

The enzyme to be used is preferably a bacterial lipase derived from Pseudomonas spp. One such enzyme that we have found to be particularly useful is "Lipase P Amano" (LPL 05518, from Amano Pharmaceutical Co. Ltd, Nagoya, Japan). Other useful enzymes include a microbial lipoprotein lipase (Genzyme).

The reaction can take place at temperatures ranging from about 30° to about 70° C., e.g. about 50° to 60° C., over a period of up to about 6 days and appears to proceed initially at the 6-position and then at the 4'-position (if both positions are free) resulting in a mixture of the 6- mono- and the 6,4'-diacylate. The two acylates can be separated e.g. by chromatography on a silica gel column, if required. Alternatively, the mixture can be chlorinated to provide sucralose, which is conveniently isolated in the form of a penta-ester and then de-esterified. Suitable methods of chlorination include those disclosed in GB 2,079,749B (Vilsmeier reagents, sulphuryl chloride), GB 2,195,632A (thionyl chloride/triphenylphosphine oxide) and in our co-pending British Patent Applications Nos. 8917468.4 and 8920600.7 (thionyl chloride/pyridine).

The following Examples illustrate the invention further:

EXAMPLE 1

Preparation of 4',6-di-O-acetylsucrose and 6-O-acetylsucrose

To a solution of sucrose (10 g) in pyridine (180 ml) was added isopropenyl acetate (60 ml) and Lipase P Amano (34 g) and the reaction mixture was maintained at 60° C. for 4 days. The enzyme was filtered off and the filtrate was concentrated to a syrup by co-distillation with toluene, then eluted through a column of silica gel with acetone followed by acetone containing 1% water to give 4',6-di-O-acetylsucrose (1 g, 8%) and 6-O-acetylsucrose (3.7 g, 33%).

Similar results were obtained when trichloroethyl acetate was used in place of isopropenyl acetate.

The structures of the 6-O-acetylsucrose and the 4',6-di-O-acetylsucrose were confirmed by $^1$H-nmr. The $^1$H-nmr spectrum of the 6-O-acetylsucrose was identical with that of authentic 6-O-acetylsucrose disclosed in GB 2,195,632A. The $^1$H-nmr spectrum of the 4',6-di-O-acetylsucrose was as follows:

$^1$H-Nmr (D$_2$O, 250 MHz): δ5.43 (d, 1H, J 3.5 Hz H-1); 5.21 (t, 1H, J 6.0 Hz, H-4'); 2.15, 2.13 (6H, 2Ac). The two acetate signals at 6 and 4' positions in the diacetate were confirmed by deuteroacetylation followed by $^1$H-nmr of the acetate signals. (C$_5$D$_5$N: C$_6$D$_6$, 1:1, 250 MHz): δ1.71 (6-Ac), 1.88 (4'-Ac). A small peak (<10%) for 1'-Ac (δ1.78) indicated that sucrose 1'-acetate was formed as a minor by-product.

EXAMPLE 2

Preparation of 4',6-di-O-acetylsucrose

To a solution of sucrose-6-acetate (10 g) in pyridine (65 ml) was added isopropenyl acetate (30 ml) and lipase P Amano (20 g) and the reaction mixture was maintained at 60° C. for 6 days. TLC showed a 1:1 mixture of 6-O-acetylsucrose and 4',6-di-O-acetylsucrose and a faster moving component, believed to be a sucrose triacetate. The enzyme was filtered off and the filtrate was concentrated to half its volume. Fresh enzyme (15 g) and pyridine (20 ml) were added and the reaction mixture was heated at 60° C. for 24 hours. TLC (ethyl acetate:acetone:water 8:6:1) indicated a yield of about 80% 4',6-di-O-acetylsucrose, with minor amounts of 6-O-acetylsucrose and two faster moving components. The enzyme was filtered off and the filtrate was concentrated to a syrup by co-distilliation with toluene, then eluted from a column of silica gel with acetone followed by acetone containing 1% water to give 4',6-di-O-acetylsucrose (5.2 g, 47%).

EXAMPLE 3

Preparation of 6-PAS from 2,3,6,3'-sucrose tetraacetate

A solution of 2,3,6,3'-tetra-O-acetylsucrose (0.5 g) (see our copending British patent application No. 8921797.0 of even date filed Sep. 27, 1988 in pyridine (1.5 ml) was treated with isopropenyl acetate (2.5 ml) and Lipase P Amano (2 g) at 60° C. for 3 days. TLC (water:ethanol:ethyl acetate, 1:5:45) revealed that about 80% of the starting material was converted into 6-PAS. The enzyme was filtered off and the filtrate was concentrated to a syrup by co-distillation with toluene, then eluted from a column of silica gel with ether to give crystalline 6-PAS (0.3 g, 55%), m.p. 150°–156° C. (from acetone-diethyl ether). The $^1$H-nmr spectrum was identical with that of authentic 6-PAS.

EXAMPLE 4

Preparation of sucrose 6-benzoate and sucrose 6,4'-dibenzoate

The procedure of Example 1 was followed except that trichloroethyl benzoate was used instead of isopropenyl acetate. The reaction gave sucrose 6-benzoate and sucrose 6,4'-dibenzoate in slightly lower yields.

EXAMPLE 5

Preparation of sucrose 6-butyrate and sucrose 6,4'-O-dibutyrate

To a solution of sucrose (10 g) in pyridine (120 ml) was added trichloroethyl butyrate (30 ml) and Lipase P Amano (34 g) and the reaction mixture was maintained at 60° C. for 4 days. TLC (acetone:water, 7:1) revealed that about 80% of the sucrose was converted into one major product and a minor faster moving product. The enzyme was filtered off and the filtrate was concentrated to a syrup by co-distillation with toluene, then eluted through a column of silica gel with acetone:water (9:0.5) to give 6,4'-di-O-butyrylsucrose (1 g, 7%) and 6-O-butyrylsucrose (4 g, 33%).

The structures of the mono- and dibutyrates were confirmed by $^1$H-nmr spectroscopy as follows:

$^1$H-Nmr. (D$_2$O, 250 MHz) of Sucrose 6-butyrate: δ5.38 (d, 1H, J$_{1,2}$ 3.7 Hz, H-1); 3.56 (dd, 1H, J$_{2,3}$ 10.0 Hz, H-2); 3.71 (t, 1H, J$_{3,4}$ 10.0 Hz, H-3); 3.43 (t, 1H,. J$_{4,5}$ 10.0 Hz, H-4), 4.21–4.42 (2H, H$_{6a}$, H$_{6b}$); 0.88 (t, 3H, J 6.0 Hz, CH$_3$); 1.62 (dd, 2H, J 5.0 Hz, CH$_2$); 2.41 (t, 2H, J 5.0 Hz, CH$_2$).

$^1$H-Nmr (D$_2$O, 250 MHz) of sucrose 4',6-dibutyrate: δ5.43 (d, 1H, J$_{1,2}$ 3.6 Hz, H-1); 3.57 (dd, 1H, J$_{2,3}$ 10.0 Hz, H-2); 3.45 (t, 1H, J$_{3',4}$ 10.0 Hz, H-4; 4.25–4.48 (m, 2H, H$_{6a}$, H$_{6b}$); 4.47 (d, 1H, J$_{3',4'}$ 8.0 Hz, H-3'); 5.24 (t, 1H, J$_{4',5'}$, 8.0 Hz, H-4'), 0.92 (d t, 6H, 2CH$_3$); 1.63 (d q, 4H, 2CH$_2$); 2.43 (d t, 4H, 2CH$_2$).

EXAMPLE 6

Conversion of sucrose 6,4'-diacetate into Sucralose

A solution of sucrose 6,4'-diacetate prepared by the method of Example 1 (100 mg) in pyridine (0.5 ml), was treated with thionyl chloride (0.2 ml) in 1,1,2-trichloroethane (1.5 ml), initially at 0° C. for 0.5 h, and then at 95° C. for 4 h. The reaction mixture was diluted with methylene chloride (20 ml), washed with cold aqueous sodium carbonate and then with water. The organic layer was dried (Na$_2$SO$_4$), concentrated by co-distillation with toluene, and then treated with 1M sodium methoxide in methanol (pH 10.0) at room temperature for 4 h. T.l.c (ethyl acetate: acetone: water, 8:6:1) revealed sucralose as the major product, which was purified by silica gel chromatography and characterised by $^1$H-Nmr spectroscopy.

We claim:

1. A sucrose 6,4'-dicarboxylic ester of an alkanoic or benzoic acid.
2. Sucrose 6,4'-diacetate.
3. Sucrose 6,4'-dibenzoate.

* * * * *